Oct. 25, 1932. P. W. MEREDITH Plant Pat. 39
BRAMBLEBERRY
Filed Nov. 30, 1931
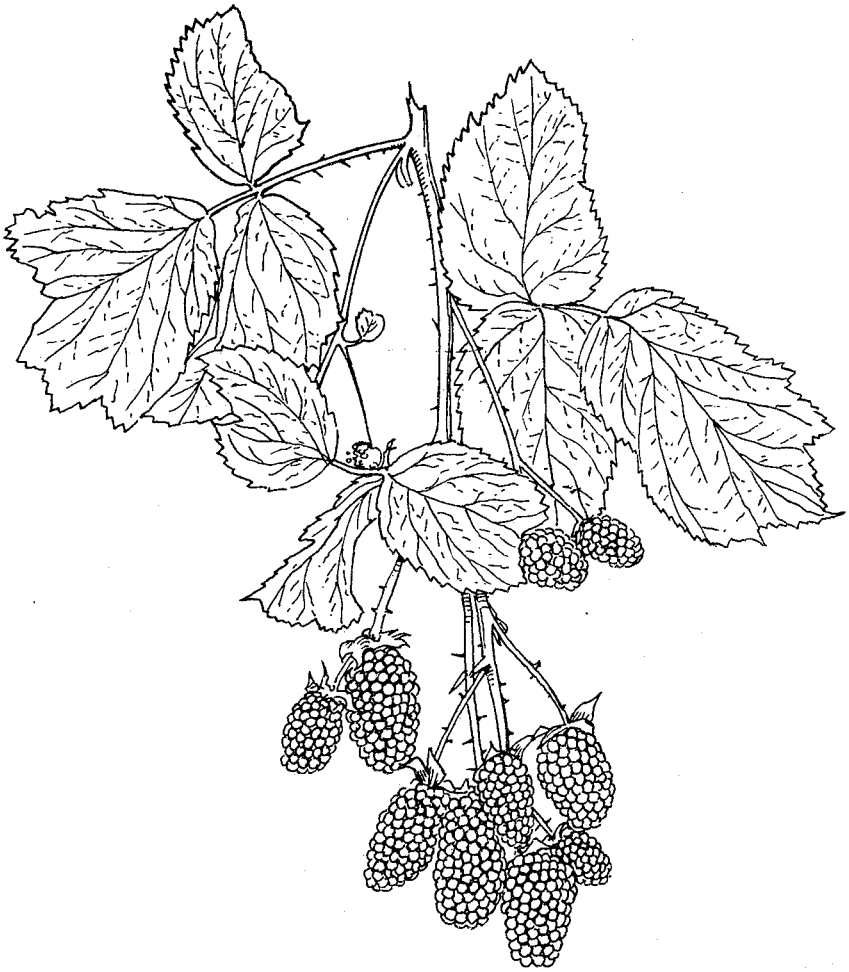
Inventor
P. W. Meredith
By Robby & Robb
Attorneys Patented Oct. 25, 1932

Plant Pat. 39

UNITED STATES PATENT OFFICE

PERCY W. MEREDITH, OF OREGON CITY, OREGON

BRAMBLEBERRY

Application filed November 30, 1931. Serial No. 578,178.

The present invention relates to a new and distinct variety of brambleberry which I discovered growing in a field of loganberries which hybrid is apparently one of the parents.

After further development of the original plant, I found that the distinctiveness of variety was maintained throughout. Owing to the resemblance to the blackberry, it is presumed that this is the other parent, although the flavor of the fruit is materially different.

From the commercial standpoint, the new variety is especially valuable because of its unusual productivity and large size. In addition, the fruit berries are comparatively unaffected by hot and dry periods in the ripening season, and do not cook on the vines as do most of the known cultivated berries. The fact that the fruit of the new variety ships far better than the longanberry greatly enhances its value. It is especially adapted for use as a canning fruit and also makes excellent pie filler, jelly, jams, wine, etc. The juice is considerably sweeter than that of the loganberry and may be readily used as are other fruit juices.

Having generally described the new variety which has been asexually reproduced, I will now more particularly set forth the prominent distinctions and characteristics which will be more clearly understood and will become apparent by reference to the accompanying drawing.

The fruit of my new brambleberry resembles the Mammoth or Cora thornless blackberry in appearance, but is materially different in flavor.

Owing to the fact that the vine trails on the ground, it resembles the loganberry in this respect rather than the blackberry which generally grows upright. The vine is larger than that of the loganberry and becomes red in color towards the tip. The canes are lavender in color near their base, resembling the loganberry in this respect.

The color of the fruit is substantially jet black and is therefore different from the longanberry. In addition, the fruit is more firm, sweeter, and less acid than the loganberry. It is distinct from the blackberry in that it possesses a loganberry or red raspberry flavor.

The color of the leaves varies with the season, and for this reason is not shown or described.

The propagation of my new brambleberry is accomplished by "tips" as in the case of the loganberry, but I have found that my new variety possesses a very great advantage in that it produces very few "suckers". As hereinbefore mentioned, it is very prolific in production. The vine is very vigorous and the plant resists disease and insects exceptionally well, having never been attacked by either since its discovery and propagation of thousands of plants.

I claim:—

A new variety of brambleberry substantially as shown and herein described.

In testimony whereof I affix my signature.

PERCY W. MEREDITH.